United States Patent
Hancock et al.

(10) Patent No.: US 9,733,145 B2
(45) Date of Patent: Aug. 15, 2017

(54) APPARATUS AND METHOD OF MEASURING COMPONENTS IN A MANUFACTURING PROCESS

(71) Applicant: Toyota Motor Engineering & Manufacturing North America, Inc., Erlanger, KY (US)

(72) Inventors: Graham William Hancock, Hamilton (CA); Ramachandran Venkata Subramanian, Kitchener (CA); Roger Ivan, Waterloo (CA)

(73) Assignee: Toyota Motor Engineering & Manufacturing North America, Inc., Erlanger, KY (US)

(*) Notice: Subject to any disclaimer, the term of this patent is extended or adjusted under 35 U.S.C. 154(b) by 613 days.

(21) Appl. No.: 14/325,367

(22) Filed: Jul. 8, 2014

(65) Prior Publication Data

US 2016/0010970 A1    Jan. 14, 2016

(51) Int. Cl.
*G01M 1/00* (2006.01)
*G01B 7/06* (2006.01)
*G01N 21/95* (2006.01)

(52) U.S. Cl.
CPC .......... *G01M 1/00* (2013.01); *G01N 21/9515* (2013.01); *G01N 2201/0221* (2013.01)

(58) Field of Classification Search
CPC ................................... G01M 1/00; G01B 7/06
USPC .................................................. 33/784, 613
See application file for complete search history.

(56) References Cited

U.S. PATENT DOCUMENTS

| | | | | |
|---|---|---|---|---|
| 4,930,096 A | * | 5/1990 | Shimizu | G01B 3/205 33/784 |
| 5,136,285 A | * | 8/1992 | Okuyama | G08C 17/02 340/3.71 |
| 5,404,317 A | * | 4/1995 | Song | G01B 3/205 702/170 |
| 5,657,550 A | * | 8/1997 | Struble | G01B 5/14 33/544.4 |
| 6,026,351 A | * | 2/2000 | Takeuchi | G01B 21/02 33/503 |

(Continued)

FOREIGN PATENT DOCUMENTS

JP          5085220 B2    9/2012

*Primary Examiner* — Christopher Fulton
(74) *Attorney, Agent, or Firm* — Christopher G. Darrow; Darrow Mustafa PC

(57) ABSTRACT

A data collection and processing system includes a handheld tool for measuring the spacing between two locations on a test object such as automobile body panels. The tool generates and transmits a measurement signal to a remote data processing unit in response to a single operator input. The data processing unit compares the measurement signal with a predetermined range of values and classifies the measurement signal as either in-range data (i.e., when the measurement falls within the range of values) or out-of-range data (i.e., when the measurement falls outside of said range of values). If the measurement signal reflects an in-range measurement, the database is updated with the measurement signal as being in/out of specification. If the measurement signal reflects an out-of-range measurement, the signal is classified as a functional flag, advancing the system to a next measurement group or confirming vehicle status (e.g., measurement complete or hold for re-work).

20 Claims, 5 Drawing Sheets

(56) References Cited

U.S. PATENT DOCUMENTS

| | | | | |
|---|---|---|---|---|
| 6,502,057 | B1 | 12/2002 | Suzuki | |
| 6,829,567 | B2* | 12/2004 | Michiwaki | H04M 11/002 340/539.11 |
| 7,275,335 | B2* | 10/2007 | Holec | G01B 5/0025 33/203.21 |
| 7,430,813 | B2* | 10/2008 | Park | B60J 10/00 33/542 |
| 2006/0162178 | A1* | 7/2006 | Freidin | G01B 3/18 33/784 |
| 2012/0203504 | A1* | 8/2012 | Jordil | G01B 3/205 702/162 |
| 2015/0059431 | A1* | 3/2015 | Lefebvre | G01B 21/042 73/1.79 |
| 2015/0100138 | A1* | 4/2015 | Laflen | G05B 13/04 700/31 |
| 2015/0219431 | A1* | 8/2015 | Jordil | G01B 21/047 33/701 |
| 2016/0119055 | A1* | 4/2016 | Nahum | H04B 7/26 455/66.1 |
| 2016/0146707 | A1* | 5/2016 | Citriniti | G06Q 10/06 702/183 |
| 2016/0173608 | A1* | 6/2016 | Laflen | H04L 67/12 702/188 |
| 2016/0173962 | A1* | 6/2016 | Vance | H04Q 9/00 340/870.02 |
| 2017/0012991 | A1* | 1/2017 | Gogada | H04L 63/105 |
| 2017/0078397 | A1* | 3/2017 | Tsubouchi | H04L 67/12 |

* cited by examiner

1

APPARATUS AND METHOD OF MEASURING COMPONENTS IN A MANUFACTURING PROCESS

TECHNICAL FIELD

The present disclosure relates to a dimensional measurement apparatus and method for a manufacturing system.

BACKGROUND

Various types of in-process and final product measurement data acquisition devices and systems are known, where each measurement device transmits data for storage and processing in a related manufacturing site. When product inspection in a mass production setting is to be performed, a plurality of varied measuring units are arranged along a production inspection line. Objects to be measured (e.g., products) flowing on the production inspection line are sequentially measured (e.g., inspected) by the respective measuring units and the measurement results are transmitted to a central controller for storage and processing to, inter alia, calculate quality levels and statistical yield of the products produced over a given interval of time (e.g., work shift).

Measurement tools capable of wirelessly transmitting data to a remote database are known. For example conventional devices employ transmitter units for measuring instruments such as calipers. Such devices allow for measurement data to be transmitted wirelessly to external data processing instruments. The transmitter unit includes a button switch which enables an operator to send control signals to a separate controller relating to measured data. Such devices do not, however, disclose control signals based upon particular measurements of the tool.

Another example describes calipers that are wirelessly connected to a computer. A controller stops transmission of output data from the measuring device to the computer when it detects that the measurement portions of the caliper are not in use. Thus, this example discloses systems that translate measurements from the caliper into control signals, but fails to disclose that the control signals are based on particular and configurable out of specification measurements, or that the control signals can indicate advancement to a next group of measurements or vehicle.

Still another example describes a sheet metal processing system that includes a first sheet metal processing machine, a first sheet metal processing machine terminal for controlling the operations of the first sheet metal processing machine, a first measuring apparatus for measuring the dimensions of a product or part processed by the first sheet metal processing machine, a second sheet metal processing machine terminal for controlling the operations of the second sheet metal processing machine, and a second measuring apparatus for measuring the dimensions of a product or part processed by the first the second sheet metal processing machine. Each terminal includes a display apparatus for displaying the sites of the part to be measured by each measuring apparatus. Each measuring apparatus includes a transmitter for transmitting the measured dimensions of the part to a receiver provided on each terminal.

Yet another example describes a receiver for receiving measurement data output as a radio wave from a measuring unit for measuring a physical or chemical value of an object to be measured together with a data type (i.e., data) for identifying the measuring unit. The measurement data and the data type received by the receiver are displayed on a display unit for a predetermined period of time and is stored in a data memory. It is confirmed whether the measurement data and the data type are properly stored, by comparing the displayed data on the display portion of the measuring unit with the displayed data on the display unit. When a cancel key of a keyboard is operated, latest measurement data and a latest data type which are stored last in the data memory are cleared. Measurement data obtained by the measuring unit and input through the keyboard and a data type assigned to the measuring unit are displayed on the display unit for a predetermined period of time and are stored in the data memory. When a transmission key of the keyboard is operated, all the measurement data stored in the data memory is output from a transmitter to an external data processing unit together with data type by radio transmission. This requires operator input to multiple input devices which may be physically separated, introducing inefficiencies in the production process.

SUMMARY

The present disclosure provides a system comprising a measurement tool capable of sending measurements wirelessly to a database. The system further includes the ability to generate control signals and process the embedded information in software without the need for an operator to interact with separate controls (e.g., a mouse or keyboard) other than the measurement tool. The system can interpret configurable "out of range" measurements as signals to advance to a next group of measurements or flag a work piece as confirmed.

According to an embodiment of the disclosure, a measurement data collection system comprises an operator hand-held tool operable to measure the dimensional separation between two target locations on a test object, to generate a measurement signal as a function of the measured dimensional separation, and to transmit the measurement signal to a remote data processing unit in response to a single operator input. The data processing unit comprises a processing unit transceiver, a memory device, and a software based processor. The data processing unit is operative to receive the measurement signal and to compare the received measurement signal with a predetermined range of measurement values stored in the memory device. The data processing unit is operative to classify and store the measurement signal as a valid data signal when said measurement falls within said predetermined range of measurement values, and is operative to classify and store the measurement signal as a functional flag signal when the measurement falls outside of the predetermined range of measurement values.

According to another embodiment of the disclosure, a measurement data collection system comprises a plurality of operator hand-held tools. Each operator hand-held tool is operable to measure the dimensional separation between two target locations on a related test object, to generate a related measurement signal as a function of the measured dimensional separation, and to transmit the measurement signal to a remote data processing unit in response to a single operator input at each operator hand-held tool. Each data processing unit comprises a processing unit transceiver, a memory device, and a software based processor. Each data processing unit is operative to receive a measurement signal from an associated operator hand-held tool and to compare the received measurement signal with an associated predetermined range of measurement values stored in the associated memory device. Each data processing unit is operative to classify and store each associated measurement signal as a valid data signal when the measurement falls within the predetermined range of measurement values, and to classify and store each measurement signal as a functional flag signal when the measurement falls outside of the predetermined range of measurement values.

A method of collecting measurement data can include the steps of providing an operator hand-held tool operable to measure the dimensional separation between two target locations on a test object. The operator hand-held tool can generate a measurement signal as a function of the measured dimensional separation. The operator hand-held tool can transmit the measurement signal to a remote data processing unit in response to a single operator input. The data processing unit comprises a processing unit transceiver, a memory device, and a software based processor, and can operate the data processing unit to receive the measurement signal and compare the received measurement signal with a predetermined range of measurement values stored in the memory device. The data processing unit can operate to classify and store the measurement signal as a valid data signal when the measurement falls within the predetermined range of measurement values, and can classify and store the measurement signal as a functional flag signal when the measurement falls outside of the predetermined range of measurement values.

These and other features and advantages of the disclosure will become apparent upon reading the following specification, which, along with the drawings, describes alternative embodiments of the disclosure in detail.

BRIEF DESCRIPTION OF THE DRAWINGS

The present apparatus and method will now be described, by way of example, with reference to the accompanying drawings, in which.

Figure 1:
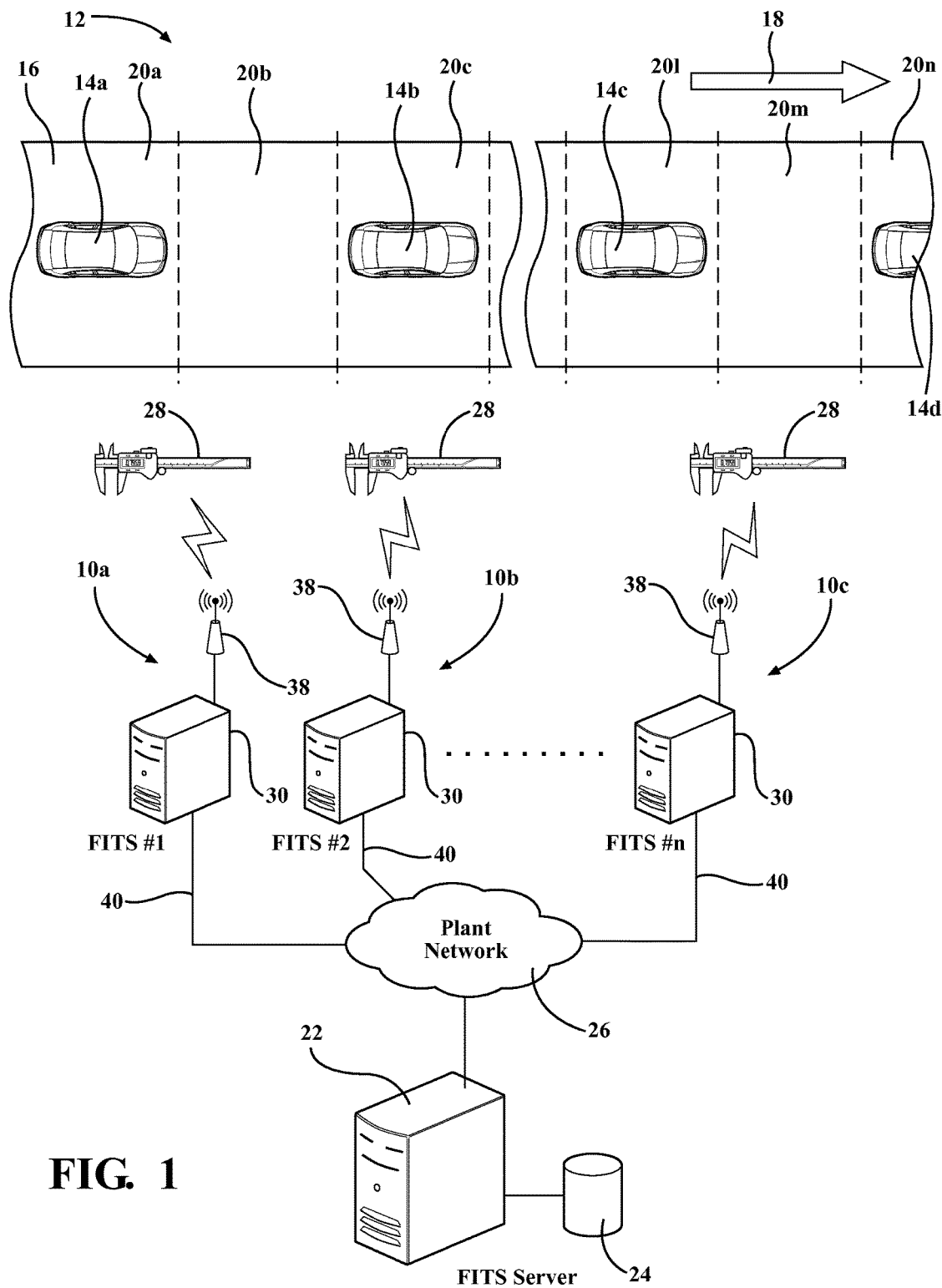
FIG. 1 is a schematic diagram of a measurement data collection system including a plurality of work stations located along a manufacturing (e.g., automobile) assembly line for measuring, processing and storing measurement data pertaining to dimensional quality, unit-to-unit consistency and conformance to design specifications of products sequentially progressing along the assembly line.

Although the drawings represent embodiments of the present apparatus and method, the drawings are not necessarily to scale and certain features may be exaggerated in order to illustrate and explain the present disclosure. The exemplification set forth herein illustrates an embodiment of the apparatus and method, in one form, and such exemplifications are not to be construed as limiting the scope of the present apparatus and method in any manner.

DETAILED DESCRIPTION

The present disclosure is embodied as a "Fit Inline Tracking System" (i.e., FITS) and provides a system comprising an operator hand-held measurement tool, such as calipers, capable of sending measurements wirelessly to a database. The system further includes the ability to generate control signals and process the embedded information in software without the need for an operator to interact with separate controls (e.g., a mouse or keyboard) other than the operator hand-held measurement tool. The system can interpret configurable out of specification measurements as signals to advance to a next group of measurements or flag a work piece as confirmed.

In certain manufacturing settings, such as automobile assembly lines, quality control team members or line workers are required to take measurements of vehicle body fit (i.e., door/hood gaps, levelness). FITS allows measurements to be wirelessly recorded into a database. This allows the responsible team member to send control signals to the software application wirelessly using a defined, configurable out of specification (i.e., spec) measurement. Although the present apparatus and method can conceivably be employed in any number of manufacturing assembly line scenarios, it will, for purposes of clarity, be described in the context of an automobile assembly line for purposes of clarity of understanding and is not to be considered as limited in that sense.

Known existing systems allow for wireless measurements to be retrieved and stored in a database but require the user to interact with the keyboard/mouse directly to control the software.

FITS improves existing technology by allowing an operator to send control signals to the data processing unit using the hand-held wireless tool employed to take the associated measurement rather than requiring him to move to the keyboard and perform the task.

In the FITS application the team member/operator takes measurements wirelessly using several tools. Each measurement point has a configurable, defined minimum (i.e., min.)/maximum (i.e., max.) value. Additionally, each measurement location is part of a logical group of measurement locations, all of which must be measured within specification (i.e., spec) or the vehicle will be flagged for further repair and/or inspection. The team member/operator may elect to skip a group measurement if he is running behind his allotted task time.

Once all measurements are complete, the team member/operator must flag the vehicle as confirmed (i.e., indicating that all measurements are complete) in order to proceed to the next vehicle. Since the wireless receiver and attached computer are in a fixed location, and the team member/operator could be located anywhere within an assigned work area or pitch, there could be a significant distance for him to move in order to proceed.

The FITS logic controller (e.g., software based device) interprets any measurement within a defined range as an action to be performed and not registered as a valid measurement. In one application, FITS interprets measurements greater than 10 mm as a signal to advance to the first measurement of the next group. After all measurements have been received and confirmation is required, if a measurement greater than 20 mm is received, FITS flags the vehicle as confirmed. This process saves the team member unnecessary movement and interaction with the computer. He can advance groups and confirm vehicles from any location in the pitch.

Measurement points are configured in a database. Data stored includes description, location on the vehicle, minimum acceptable value and maximum acceptable value.

The FITS logic controller interprets any measurement within a defined range as an action to be performed and not registered as a valid measurement. In the FITS application, the range of allowable measurement values on the vehicle is between −2.5 and 8 mm. Therefore, any measurement greater than 10 mm will be considered an invalid measurement. FITS uses measurements greater than 10 mm to advance to the first measurement of the next group. After all measurements have been received and confirmation is required, if a measurement larger than 20 mm is received, FITS flags the vehicle as confirmed.

A main feature of the present disclosure is to reduce the burden of additional motion on the team member/operator by eliminating the need to walk to the workstation and operate the mouse or keyboard. The team member/operator can control the application using the wireless measurement tool from anywhere in the pitch and is not required to carry any extra equipment or tools.

Referring to FIG. 1, a plurality of measurement data collection systems 10a-10c are associated with an automobile assembly line 12 including a stream of in-process automobiles 14a-14d (e.g., body only or on rolling chassis) traveling along a defined pathway 16 in a synchronized manner as indicated by an arrow 18. As the automobiles 14 traverse the pathway 16 they successively enter and exit defined work stations 20a-20n. Each work station 20a-20n (i.e., pitch) has a defined function such as a specific assembly step or performing a quality control check. Work stations 20b, 20c and 20l are designated for quality control purposes and are equipped with autonomous measurement data collection systems 10a, 10b and 10c, respectively. Each of said measurement data collection systems 10a, 10b and 10c communicates with a central host server 22 (e.g., FITS server) and memory storage device 24 (e.g., database) via a plant data communication network 26.

Measurement data collection system 10b is typical of the three systems 10a, 10b and 10c illustrated in FIG. 1 and will be described in greater detail herein with the understanding that the composition and functionality of measurement data collection systems 10a, 10b and 10c are common.

Measurement data collection system 10b comprises an operator hand-held tool 28 and a dedicated data processing unit 30 communicating with the central host server 22 via the plant network 26.

Figure 1A:
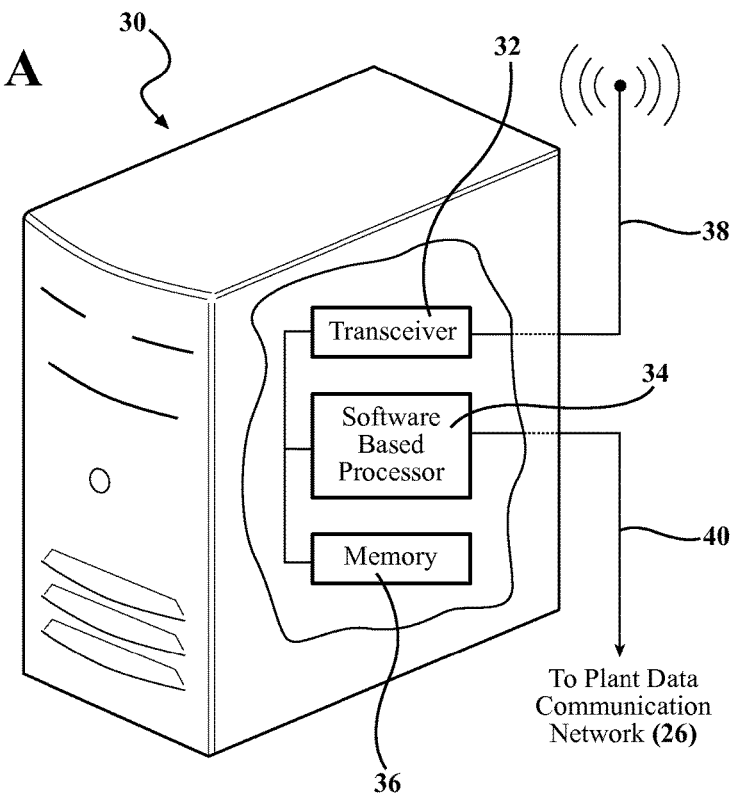
FIG. 1A is a schematic diagram of one of the three data processing units depicted in FIG. 1 on an enlarged scale.

Referring to FIG. 1A, each data processing unit 30 includes a radio frequency (i.e., RF) transceiver 32 interconnected with a logic based processor 34 (e.g., software based processor) and a memory device 36. The RF transceiver 32 includes an antenna 38 for communication with the operator hand-held tool 28. The software based processor 34 includes a data line 40 for communicating with the FITS server 22 via the plant data communication network 26.

Figure 3:
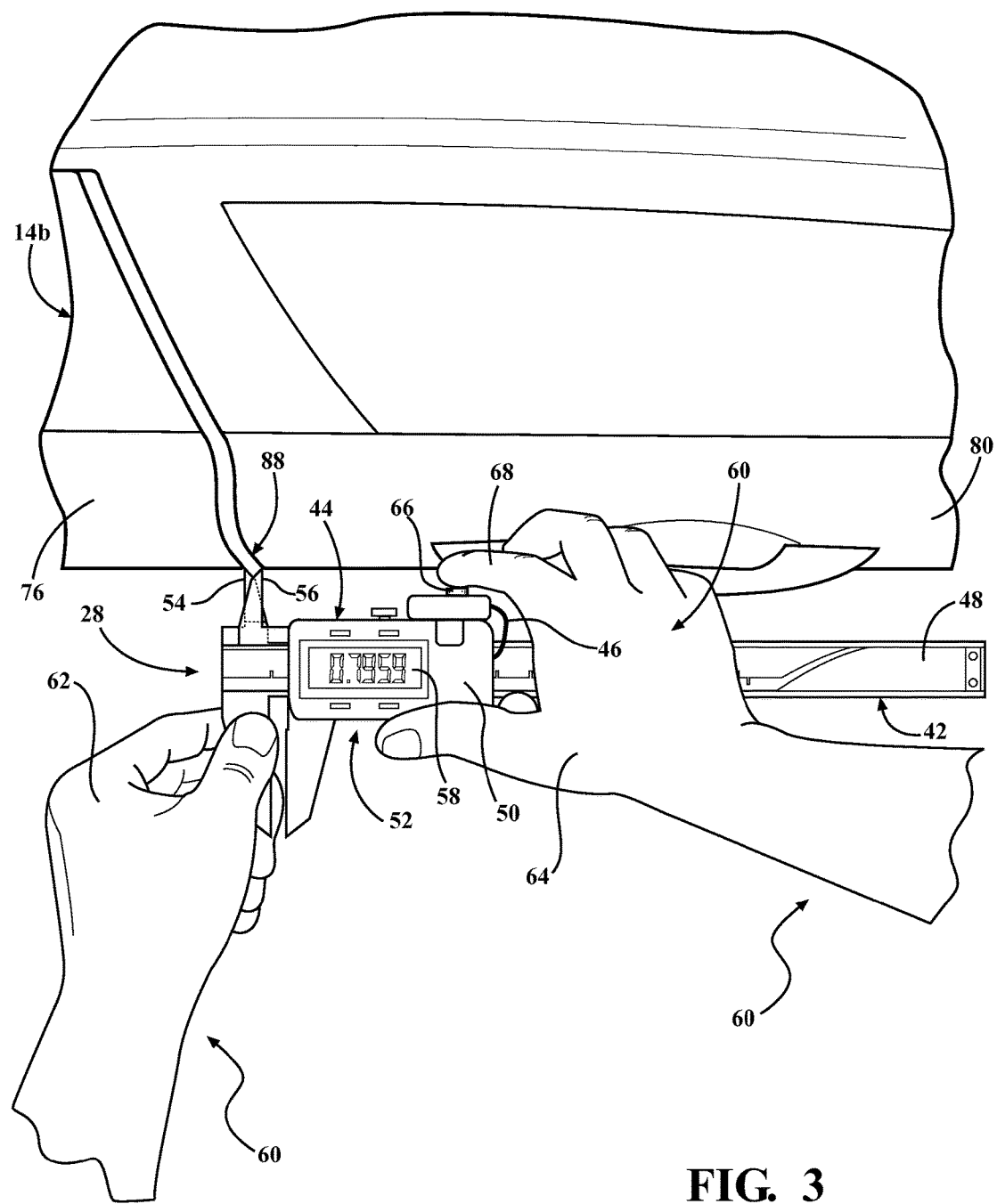
FIG. 3 is a diagram of a line worker manipulating a hand-held digital caliper measurement tool at one of the work stations illustrated in the system of FIG. 1 for inputting certain product dimensional measurements, and wirelessly transmitting the measurement data signals to system processor and memory devices.

Referring to FIG. 3, the operator hand-held tool 28 comprises an electric vernier caliper 42 and a transceiver unit 44 connected through a connection cable 46. The electric vernier caliper 42 consists of a main beam 48, a slider 50 movable along the main beam 48, and an encoder 52 that detects a displacement of the slider 50 relative to the main beam 48 as an electric signal. The main beam 48 includes an inside measuring jaw 54 which is provided at one end (in longitudinal direction) of the main beam 48. The slider 50 includes an inside measuring jaw 56 which is provided on an end of the slider 50 in alignment with the inside measuring jaw 54 of the main beam 48. The slider 50 also includes a display unit 58 that displays a measurement result and/or a feedback signal from the data processing unit 30.

Referring to FIGS. 1 and 3, an operator 60 assigned to work within work station 20c manipulates the operator hand-held tool 28 by grasping the main beam 48 with one hand 62 (e.g., left hand) and the slider 50 with the other hand 64 (e.g., right hand) and slidingly repositioning the slider 50 along the main beam 48 to effect one of a series of measurements.

The transceiver unit 44 of the operator hand-held tool 28 also comprises an operator input device such as a transmit actuation device 66 (e.g., push-button switch) located under an index finger 68 of the operator's other hand 64. Whenever the push button switch is pressed by the operator 60, the transceiver unit 44 of the operator hand-held tool 28 generates and transmits a measurement signal as a function of the actual (i.e., measured) separation between the main beam inside measuring jaw 54 and the slider inside measuring jaw 56 to the remotely located data processing unit 30.

Figure 2:
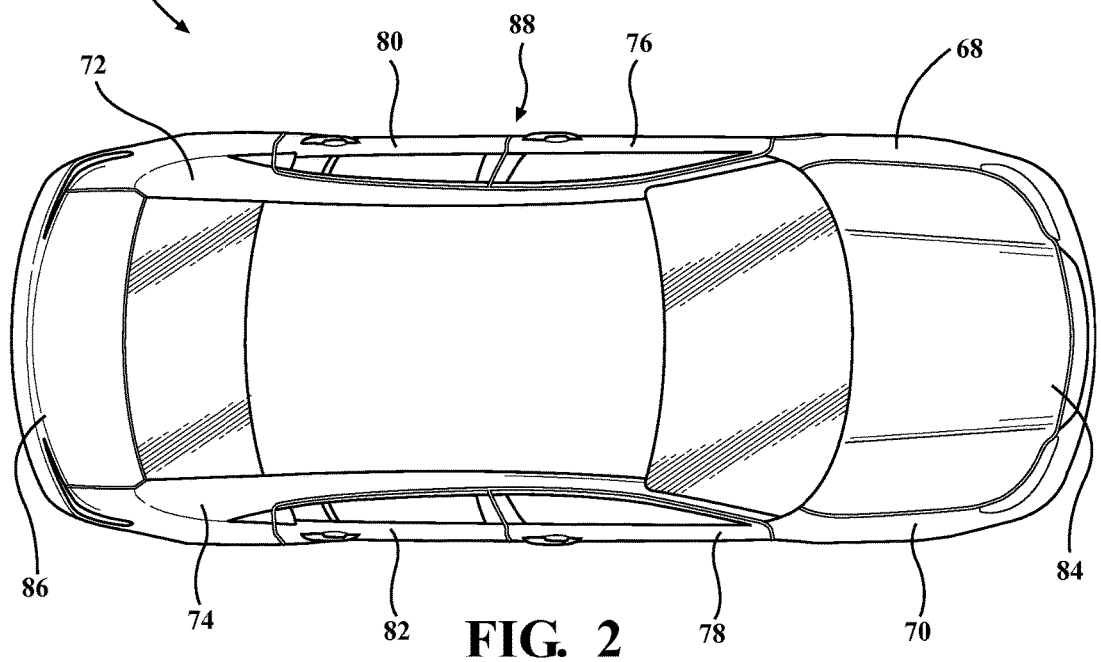
FIG. 2 is an overhead view of an automobile being conveyed on the assembly line of FIG. 1, on an enlarged scale, depicting features suitable for measurement by the measurement data collection system.

Referring to FIG. 2, the in-process automobile 14b located in work station 20c is illustrated on an enlarged scale depicting typical measurement points (e.g., target locations) for the operator 60 to measure. Automobile 14b includes a left-front fender 68, a right-front fender 70, a left-rear fender 72, a right-rear fender 74, a left-front door 76, a right-front door 78, a left-rear door 80, a right-rear door 82, a hood panel 84 and a trunk panel 86.

Inasmuch as adjacent pairs of fenders, doors and panels are relatively displaceable in application, precise alignment and interfit is critical for both functionality and appearance aspects of overall quality. Restated, uniformity in spacing between adjacent vehicle panels is deemed to be desirable in the overall quality control process.

Figure 4:
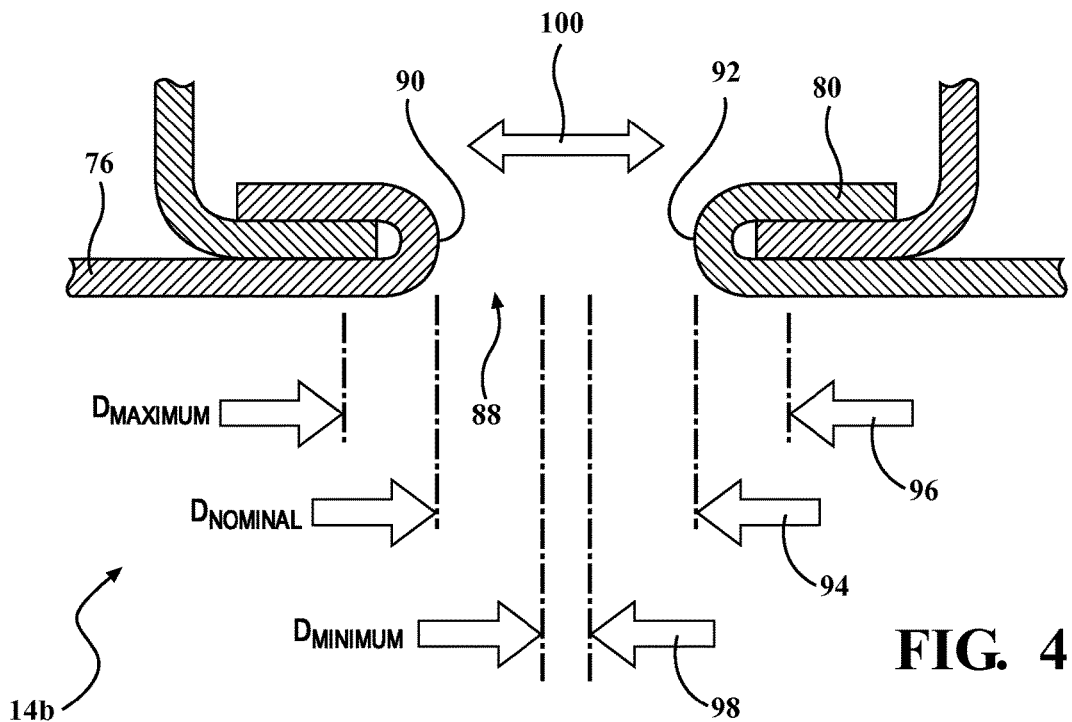
FIG. 4 is an illustration of a broken, cross-sectional portion of a product feature being measured by a digital caliper tool of the present disclosure, on a greatly enlarged scale.

Referring to FIG. 4, a detailed example of a point of measurement 88 on the outer body of the automobile 14b (e.g., the test object) is illustrated. Specifically, the exemplar measurement is the space between a rear vertical edge 90 of the left-front door 76 (e.g., the first target location) and a front vertical edge 92 of the left-rear door 80 (e.g., the second target location) at a predetermined vertical location or elevation. The ideal or nominal dimensional separation (i.e., $D_{nom}$) is indicated by opposed arrows 94. The maximum dimensional separation (i.e., $D_{max}$) is indicated by opposed arrows 96. The minimum dimensional separation (i.e., $D_{min}$) is indicated by opposed arrows 98. Normal unit-to-unit dimensional variances are indicated by arrow 100.

To obtain a valid measurement of the dimensional separation between the rear vertical edge 90 of the left-front door 76 and the front vertical edge 92 of the left-rear door 80, the operator 60 manipulates the slider 50 to align the inside measuring jaw 56 of the slider 50 with the inside measuring jaw 54 of the main beam 48. The operator 60 then extends the aligned measuring jaws 54 and 56 within the point of measurement 88. Next, the operator 60 manipulates the slider 50 away from the main beam inside measuring jaw 54 until the main beam inside measuring jaw 54 assumes point contact with the rear vertical edge 90 of the left-front door 76 and the slider inside measuring jaw 56 assumes point contact with the front vertical edge 92 of the left-rear door 80. Finally, the operator 60 presses the push button switch 66. Upon pressing the push button switch 66, the transceiver unit 44 wirelessly broadcasts a measurement signal to the data processing unit 30.

Figure 5:
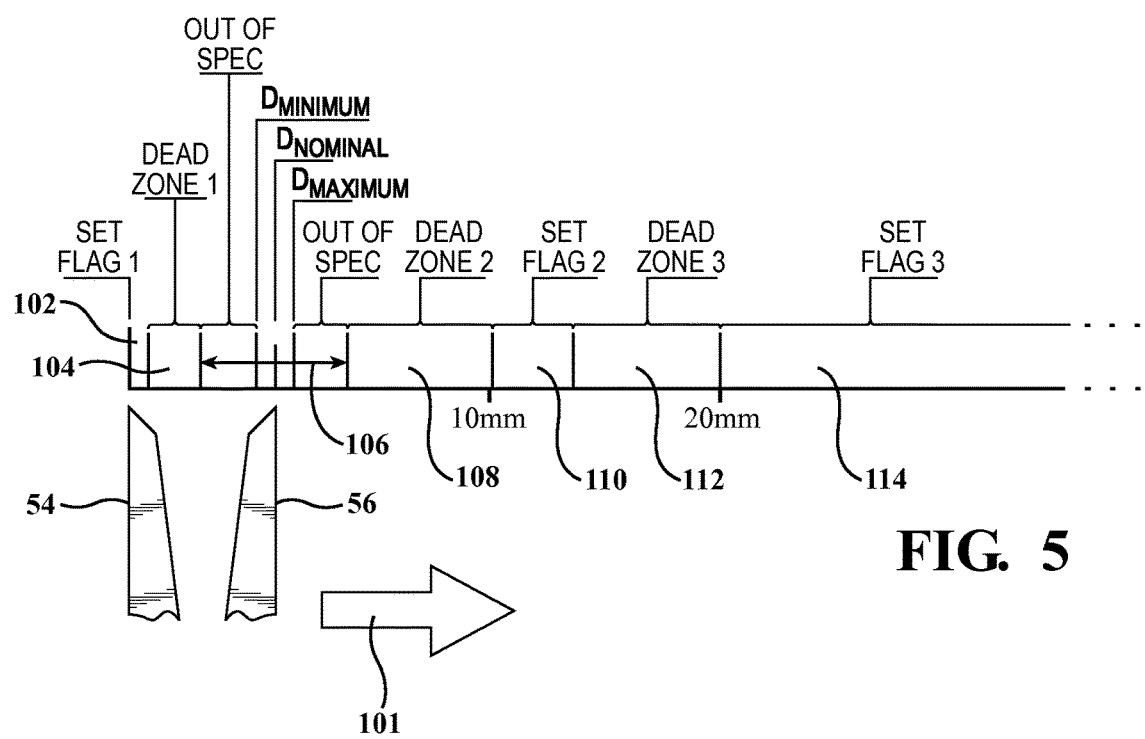
FIG. 5 is a graphical illustration of the functional operability of the measurement probes of the digital caliper tool of FIG. 3 throughout their extended range of relative displacement.

Referring to FIG. 5, although a measurement signal is transmitted by the operator hand-held tool 28 each time the push button switch 66 is depressed by the operator 60, each measurement signal may be interpreted differently by data processing unit 30, depending upon which range of measurement values stored in the memory device into which the measurement signal falls.

A number of distinct measurement value ranges are defined and/or stored within the data processing unit 30 beginning at a corresponding null measurement value of the electric vernier caliper 42 and extending serially throughout the full extent of the main beam 48. A first measurement value range 102 corresponds with a first set flag function range. A second measurement value range 104 corresponds with a first dead zone range. A third measurement value range 106 corresponds with a combined out-of-spec$_{min}$, maximum dimensional separation ($D_{max}$) and out-of-spec$_{min}$ range. A fourth measurement value range 108 corresponds with a second dead zone range. A fifth measurement value range 110 corresponds with a second set flag function range. A sixth measurement value range 112 corresponds with a third dead zone range. A seventh measurement value range 114 is open ended and corresponds with a third set flag function range.

In the embodiment of the disclosure of FIG. 5, the measurement data collection system 10 operates to interpret each measurement signal received from the operator hand-held tool 28 as either a valid data signal (i.e., falling within a target value range) or something else. If a measurement data signal is determined to be a valid data signal falling within the $D_{max}$ to $D_{min}$ value range, it is so classified and stored in the memory device 36, and a confirmatory reply sent to the operator 60. If a measurement data signal is determined to not be a valid data signal falling outside of the $D_{max}$ to $D_{min}$ value range, it is classified and stored in the memory device 36 as an out-of-spec measurement, and an advisory reply sent to the operator 60 for follow-up action.

If a measurement data signal is determined to not be a valid data signal, falling within the second measurement value range 104 (first dead zone range), the fourth measurement value range 108 (second dead zone range), or the sixth measurement value range 112 (third dead zone range), the data processing unit will take no further action, assuming that the measurement data signal is erroneous. No data will be stored.

If a measurement data signal is determined to not be a valid data signal, falling within the first measurement value range 102 (first set flag function), the fifth measurement value range 110 (second set flag function), or the seventh measurement value range 114 (third set flag function), the data processing unit 30 will initiate a pre-established logic control process (e.g., software subroutine) within the software based processor 34 to effect a specific action such as repeat the previous valid measurement, skip forward to the next grouping of measurements, or flag the automobile 14 being measured for follow-up or off-line inspection. If a measurement data signal is determined to not be a valid data signal, falling within the first measurement value range 102, the fifth measurement range 110, or the seventh measurement range 114, it is classified and stored in the memory device 36 as a functional flag signal.

Figure 6:
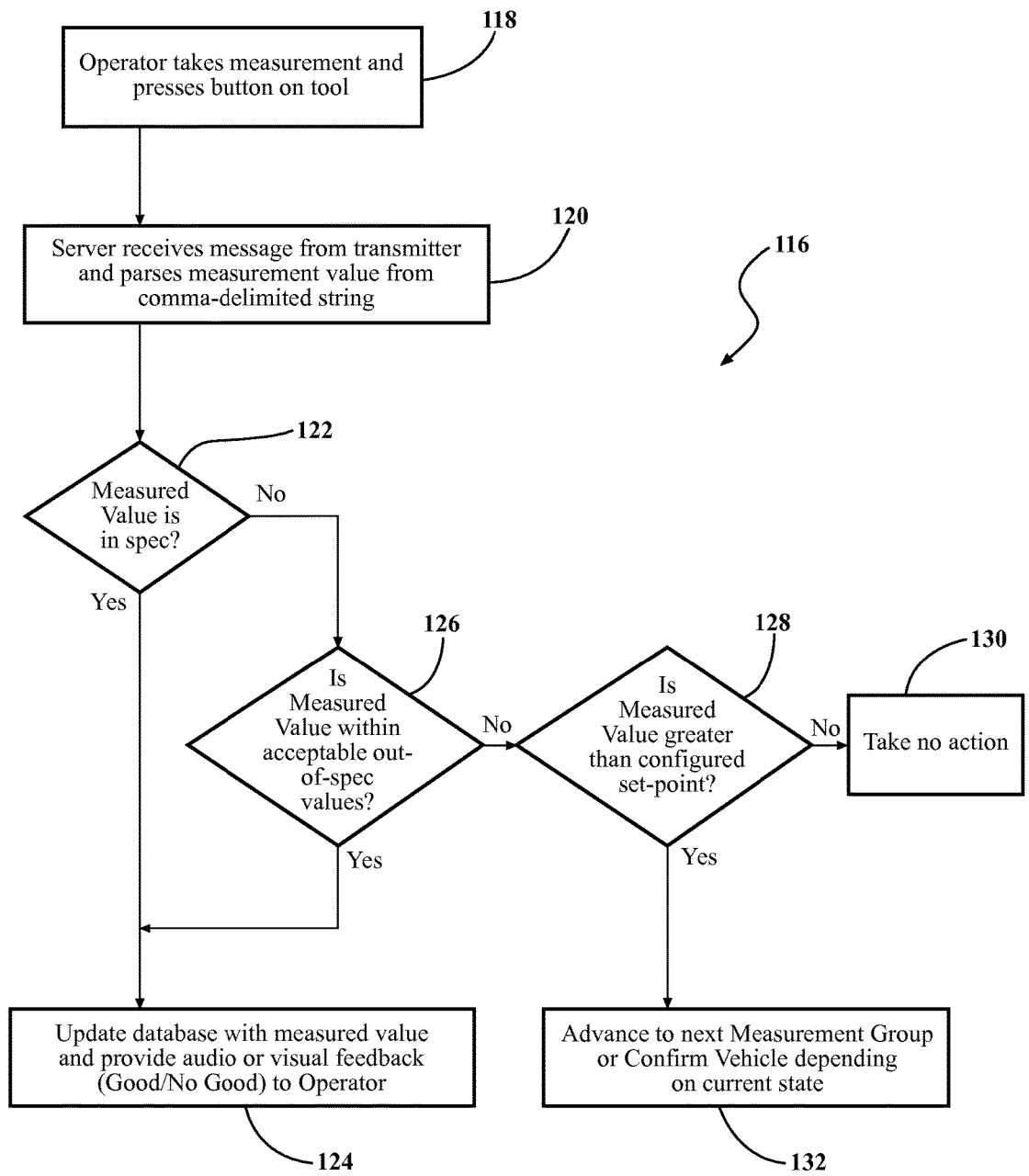
FIG. 6 is an application software logic flow diagram of one of the data collection work stations of the present disclosure.

Referring to FIG. 6, an application software logic flow diagram 116 of one of the measurement data collection systems 10 of the present disclosure is initiated at step 118 where the operator 60 takes a measurement and presses the push button switch 66 on the operator hand-held tool 28. Thereafter, the data processing unit 30 receives a message from the operator hand-held tool 28 and parses the measurement value from a comma-delimited data string at step 120. Next, at a logical step 122, if the measurement signal is in-spec, the memory device 36 is updated with the measured value and the operator 60 receives a visual or audio feedback via the operator hand-held tool 28 at step 124. Alternately, at logical step 126, if the measurement signal is within acceptable out-of-spec values, the database 36 is updated with the measured value and the operator 60 receives a visual, tactile or audio feedback via the operator hand-held tool 28 at step 124. Alternately, at logical step 126, if the measured value is not within acceptable out-of-spec values, logical step 128 determines if the measured value is greater than a configured set-point. If the measured value is not greater than the configured set-point, no action is taken at step 130. Alternately, if the measured value is greater than the configured set-point, the data processing unit 30 advances to a next measurement group or confirms the automobile 14b depending on the current state at step 132.

It is to be understood that the present apparatus and method has been described with reference to specific embodiments and variations to provide the features and advantages previously described and that the embodiments are susceptible of modification as will be apparent to those skilled in the art.

Furthermore, it is contemplated that many alternative, common inexpensive materials can be employed to construct the basis constituent components. Accordingly, the forgoing is not to be construed in a limiting sense.

The present apparatus and method has been described in an illustrative manner, and it is to be understood that the terminology, which has been used is intended to be in the nature of words of description rather than of limitation.

Obviously, many modifications and variations of the present invention are possible in light of the above teachings. For example, the operator hand-held tool could comprise a levelness sensor (not illustrated) or cooperating outside measuring jaws (not illustrated) carried on the main beam 48 and the slider 50. It is, therefore, to be understood that within the scope of the appended claims, wherein reference numerals are merely for illustrative purposes and convenience and are not in any way limiting, the present apparatus and method, which is defined by the following claims as interpreted according to the principles of patent law, including the Doctrine of Equivalents, may be practiced otherwise than is specifically described.

The invention claimed is:

1. A measurement data collection system comprising:
an operator hand-held tool operable to measure a dimensional separation between two target locations on a test object, to generate a measurement signal as a function of said measured dimensional separation, and to transmit said measurement signal to a remote data processing unit in response to an operator input,
said data processing unit comprising a processing unit transceiver, a memory device, and a logic based processor, said data processing unit operative to receive said measurement signal and to compare said received measurement signal with a predetermined range of measurement values stored in said memory device, said data processing unit operative to classify and store said received measurement signal as a valid data signal when said received measurement signal falls within said predetermined range of measurement values, and to classify and store said received measurement signal as a functional flag signal when said received measurement signal falls outside of said predetermined range of measurement values.

2. The measurement data collection system of claim 1, wherein said operator hand-held tool comprises an electric vernier caliper or a levelness tool operatively coupled with a wireless transceiver configured for two-way communication with said processing unit transceiver.

3. The measurement data collection system of claim 1, wherein said operator hand-held tool comprises a transmit actuation device operable to effect said transmission of said measurement signal in response to said operator input.

4. The measurement data collection system of claim 1, wherein said operator hand-held tool comprises a transmit actuation device operable to effect transmission of said operator input.

5. The measurement data collection system of claim 4, wherein said transmit actuation device comprises a single push button switch.

6. The measurement data collection system of claim 1, wherein said data processing unit is operative to transmit said stored valid data signal or said stored functional flag signal to a central host server.

7. The measurement data collection system of claim 1, wherein said data processing unit is operative to transmit said stored valid data signal or said stored functional flag signal to said operator hand-held tool.

8. The measurement data collection system of claim 7, wherein said operator hand-held tool comprises an operator perceptible display configured to alert an operator of the receipt of said stored valid data signal or said stored functional flag signal.

9. The measurement data collection system of claim 8, wherein said operator perceptible display comprises at least one of a visual display, an audible display or a tactile display.

10. The measurement data collection system of claim 1, wherein said data processing unit is dedicated to said operator hand-held tool.

11. The measurement data collection system of claim 1, wherein test object comprises an automobile body.

12. The measurement data collection system of claim 11, wherein said two target locations are disposed on respective edges of adjacent panels of said automobile body.

13. The measurement data collection system of claim 1, wherein said processing unit transceiver comprises a radio frequency transceiver.

14. The measurement data collection system of claim 1, wherein said predetermined range of measurement values comprises at least one target range of measurement values.

15. The measurement data collection system of claim 14, wherein said data processing unit is operative to compare said received measurement signal with a second range of measurement values stored in said memory device, and to disregard said received measurement signal when said received measurement signal falls within said second range of measurement values.

16. The measurement data collection system of claim 15, wherein said second range of measurement values comprises at least one dead zone range of measurement values.

17. The measurement data collection system of claim 14, wherein said data processing unit is operative to compare said received measurement signal with a third range of measurement values stored in said memory device, and to classify and store said received measurement signal as a functional flag signal when said received measurement signal falls within said third range of measurement values.

18. The measurement data collection system of claim 17, wherein said third range of measurement values comprises at least one set flag function range of measurement values.

19. A measurement data collection system comprising:
a plurality of operator hand-held tools, each operator hand-held tool operable to measure a dimensional separation between two target locations on a test object, to generate a measurement signal as a function of said measured dimensional separation, and to transmit said measurement signal to a remote data processing unit in response to a single operator input,
said data processing unit comprising a processing unit transceiver, a memory device, and a logic based processor, said data processing unit operative to receive each said measurement signal from each said operator hand-held tool and to compare each said received measurement signal with an associated predetermined range of measurement values stored in said memory device,
said data processing unit operative to classify and store each said received measurement signal as a valid data signal when said received measurement signal falls within said predetermined range of measurement values, and to classify and store each said received measurement signal as a functional flag signal when said received measurement signal falls outside of said predetermined range of measurement values.

20. A method of collecting measurement data comprising the steps of:
providing an operator hand-held tool operable to measure a dimensional separation between two target locations on a test object;
generating a measurement signal as a function of said measured dimensional separation;
transmitting said measurement signal to a remote data processing unit in response to a single operator input;
said data processing unit comprising a processing unit transceiver, a memory device, and a logic based processor;
operating said data processing unit to receive said measurement signal and to compare said received measurement signal with a predetermined range of measurement values stored in said memory device; and
operating said data processing unit to classify and store said received measurement signal as a valid data signal when said received measurement signal falls within said predetermined range of measurement values, and to classify and store said received measurement signal as a functional flag signal when said received measurement signal falls outside of said predetermined range of measurement values.

* * * * *